United States Patent [19]
Alas et al.

[11] Patent Number: 6,018,057
[45] Date of Patent: Jan. 25, 2000

[54] PROCESS FOR PRODUCING ACID ANHYDRIDES

[75] Inventors: Michel Alas, Melle; Michel Gubelmann, Lyons; Jean-Michel Popa, Drancy, all of France

[73] Assignee: Rhodia Chimie, Courbevoie Cedex, France

[21] Appl. No.: 08/086,885

[22] Filed: Jul. 7, 1993

Related U.S. Application Data

[63] Continuation of application No. 07/870,773, Apr. 21, 1992, Pat. No. 5,260,456, which is a continuation of application No. 07/524,880, May 18, 1990, abandoned, which is a continuation-in-part of application No. 07/272,793, Nov. 18, 1988, abandoned.

[30] Foreign Application Priority Data

Nov. 20, 1987 [FR] France ................................. 87 16065

[51] Int. Cl.$^7$ ................................................. C07D 305/00
[52] U.S. Cl. .......................... 549/231; 549/233; 549/239; 549/245; 549/247; 549/262
[58] Field of Search ..................... 549/231, 233, 549/239, 245, 247, 262; 502/81, 82, 83

[56] References Cited

U.S. PATENT DOCUMENTS 2,981,697  4/1961  Mickelson et al. ....................... 502/82
3,704,329  11/1972  Rindtorff et al. ....................... 568/896

FOREIGN PATENT DOCUMENTS 801722    9/1958   United Kingdom .
854999    11/1960  United Kingdom .
81/01844  7/1981   WIPO ..................................... 502/81

OTHER PUBLICATIONS

McCabe et al., Clay–and Zeolite–catalysed Cyclic Anhydride Formation, 356 J.Chem.Research (S), 1985 pp. 356–357.

Franz et al., Katalysatoren auf der Basis saureaktivierter Bentonite, Erdol und Kohle, 12 Jahrg./Mai 1959, Nr. 5, pp. 335–339.

Gunther, Chem. Abs. vol. 55, 25 234b (1961).

Notification from European Patent Office, Feb. 4, 1991 with attached Rapport De Recherche Europeenne, EP 88 40 2809.

Cram and Hammond, Organic Chemistry, McGraw–Hill, pp. 310–311 (1959).

*Primary Examiner*—Bernard Dentz
*Attorney, Agent, or Firm*—Finnegan, Henderson, Farabow, Garrett & Dunner, L.L.P.

[57]  ABSTRACT

A process for producing anhydrides by passing a solution of the acid, preferably an organic polyacid, which is to undergo anhydridation over an acidified clay and a process for producing the catalysts therefor.

20 Claims, No Drawings

PROCESS FOR PRODUCING ACID ANHYDRIDES

This is a continuation of Ser. No. 07/870,773 filed Apr. 21, 1992, now U.S. Pat. No. 5,250,456, which is a continuation of Ser. No. 07/524,880 filed May 18, 1990 now abandoned, which is a continuation-in-part of Ser. No. 07/272,793 filed Nov. 18, 1988, now abandoned.

The present invention relates to a process for producing acid anhydrides and catalysts therefor. More specifically, it relates to a process for producing internal anhydrides, such as itaconic acid anhydride, from organic polyacids. It also relates to a new catalyst for such processes. It is an aim of the present invention to produce itaconic anhydride from itaconic acid with a low production of citraconic acid.

The preparation of itaconic anhydride by exchange between itaconic acid and acetic anhydride using the conventional processes of transanhydridation, is known from the prior art. This process has the disadvantage of using a raw material which is expensive, namely acetic anhydride, with the formation of a by-product which must be eliminated, i.e., acetic acid. The reaction is further limited as to the temperature which can be used to avoid initiating a polymerization reaction. A temperature below 75° C. is essential. The yields obtained by this process do not exceed 90% of itaconic anhydride. Moreover, the industry has for a long time been seeking to carry out anhydridation of itaconic acid directly from the acid without the necessity of using another anhydride, such as acetic anhydride.

It has also been disclosed in the article which appeared in J. Chem. Research (S) 1985, 356–357, that itaconic anhydride can be produced by passing itaconic acid over a proprietary clay of the type exemplified by TONSIL 13 from Sud-Chemie (Munich) treated with an aluminum salt. This technique employs clays which have been exchanged with an aluminum salt. On the one hand, this has the disadvantage that the natural clay requires a quite elaborate treatment which increases the cost of producing the anhydride. A noteworthy, but not necessarily advantageous, feature of this technique is that the double bond of the itaconic molecule is stable under the reaction conditions, contrary to the usual catalytic rearrangement of itaconic acid into citraconic acid. Among the disadvantages of the catalyst disclosed in the above-identified paper are the following:

the catalyst reverts to a less active form within a relatively short time;

it is costly to prepare and produces many dirty effluents;

the catalyst needs water to be active, thus it is not useful in reactions which are conducted in such a way as to remove water;

the catalyst is not versatile and is not able to easily cyclize common di-acids in common solvents; and more specifically, the catalyst is active only on five-membered rings.

It is an object of the present invention to provide a new process for producing acid anhydrides which avoids the disadvantages of previously-known processes. A further object of the present invention is to provide a new catalyst for the cyclization of di-acid to form internal anhydride.

Additional objects and advantages of the invention will be set forth in the description which follows, and in part will be apparent from the description, or may be learned by practice of the invention. The objects and advantages of the invention may be realized and obtained by means of the instrumentalities and combinations particularly pointed out in the appended claims.

To achieve the foregoing objects, and in accordance with the purposes of the invention as embodied and broadly described herein, there is provided a process for producing acid anhydrides which comprises bringing into contact, for a period of time sufficient to produce the acid anhydride, an acid, preferably an organic polyacid and more preferably, a polycarboxylic acid, which is to undergo anhydridation and a clay which has undergone one or more treatments by one or more compounds, preferably acids or ammonium salts, capable of providing an H+ ion to the clay. The invention also relates to a process for producing an acid anhydride which comprises bringing into contact, for a period of time sufficient to produce the acid anhydride, an acid which is to undergo anhydridation and a clay containing H+ ions in an amount sufficient to effect anhydridation.

Clays which can be used in the process of the present invention are preferably selected from natural clays having a structure known as "TOT" or tetrahedron-octahedron-tetrahedron.

These clays are divided into three classes:

smectites;

vermiculites; and micas.

"TOT" clays occur in the form of simple lamellae comprising two layers of oxygen atoms in tetrahedral positions surrounding silicon atoms, separated by one layer of oxygen atoms in octahedral positions surrounding the metal M of the type $(MO_4OH_2)$ where M is a di- or trivalent cation.

When the tetrahedra are occupied by $Si^{iv}$ species, the electrical neutrality of the lamella is maintained in two ways, depending on the charge of the cation occupying the octahedra;

if it is divalent ($Mg^{+2}$, $Fe^{+2}$, . . . ), all the octahedral cavities are occupied. The lamella is then called trioctahedral.

if it is trivalent ($Al^{+3}$, $Fe^{+3}$, . . . ), two octahedral cavities out of three are occupied and the lamella is called dioctahedral.

However, numerous substitutions are possible, in both the tetrahedral layer and the octahedral layer. These can produce an excess of negative charge in the lamella. Neutrality of the crystal is then achieved by compensating cations being inserted between the lamellae.

Among clays of the "TOT" type defined above, smectites are preferably used.

Smectites are classified according to the nature of the metal M (aluminum, magnesium iron, lithium) and the nature of the compensating cation (sodium, potassium, calcium).

Among the class of smectites can be mentioned:

montmorillonites of the formula $Si_4(Al_{z-x}—Mg_x)O_{10}(OH)_2, M+_x$ beidellites of the formula $(Si_{4-x}Al_x)Al_2O_{10}(OH)_2 1\ M+_x$
nontronites of the formula $(Si_{4-x}Al_x)Fe_2O_{10}(OH)_2, M+_x$
hectorites of the formula $Si_4(Mg_{3-x}Li_x)O_{10}(OH)_2, M+_x$
stevensites of the formula $Si_4(Mg_{3-x})O10(OH)_2, M+_x$
saponites of the formula $(Si_{4-x}Al_x)Mg_3O_{10}(OH)_2, M+_x$
fluorohectorites of the formula $Si_4(Al_{2-x}—Li_x)O_{10}(F,OH)_2, M+_x$ sauconites of the formula $(Si_{4-x}Al_x)$ $(Mg_{3-x}Zn_x)O_{10}(OH)_2, M+_x$ Among the smectites, the montmorillonites are particularly preferred for use within the scope of the present invention. Moreover, among the montmorillonites are proprietary clays which are already acidic. For example, the following clays can be used:

° product KSF, marketed by Sud-Chemie (Munich),

° product K 10 marketed by Sud-Chemie.

Clay KSF has a surface area of 20 to 40 m²/g and a density of 800 to 850 g/l.

Clay K 10 has a surface area of 220 to 270 m²/g and a density of 300 to 370 g/l.

Acidic clays, as is, can be used in one embodiment of the invention or can be treated to increase the H+ ion content in another embodiment of the invention. In one preferred process according to the invention, the clay is subjected to an acid treatment using an aqueous solution of an acid. Depending on the particular clay, it may be necessary to repeat the acid treatment. Sometimes, for example, two to five repetitions of the acid treatment are required. To be sure that a good acidity of the clay is reached, the acid treatment is repeated until there is no significant change in the pH of the aqueous medium. Another way to reach that point is to acidify the clay by the way of a buffered solution or to use an ion exchanger.

Among the acids used for the acid solution, particularly preferred are hydrochloric acid, sulfuric acid, nitric acid, perchloric acid and phosphoric acid. Organic acids can also be used, particularly trifluoromethanesulfonic acid, but they have no advantage in relation to inorganic acids and have the disadvantage of being more expensive.

The treatment is carried out in an aqueous medium, generally in water with a pH range from 1.5 to 2.5 and lower than 7. The preferred pH ranges from 2 to 4.

The source of H+ ion is of rather little importance when the above range is reached. The protonic source may be a solid or liquid ion exchanger. Ion exchanger resins such as sulfonic group resins or nafion are preferred. Usually, the protonic source is a water-soluble strong mineral and/or organic acid where the acid has a pKa lower than 4.

The concentration of the aqueous acid solution may be varied, but it preferably has a pH not below 2 so as not to destroy the clay, and contains a quantity of H+ ions, expressed in milliequivalents, corresponding at least to the exchange capacity of the clay. The exchange capacity (charge per half matrix) of a clay is defined as the number of cations, expressed in milliequivalents, which can be exchanged on a 100 g sample.

This exchange capacity varies for smectites in the range of 0.2 to 0.6 and for vermiculites in the range of 0.6 to 0.9. It is, however, preferable within the scope of the present invention to use a solution of acid containing as many H+ equivalents as there are cations to be exchanged in the clay, e.g., containing at least 0.2 to 0.6 H+ per half matrix for smectite clay, that is at least 50 to 150 milliequivalents of acid to 100 g of smectite clay.

The preferred catalysts are those wherein the clay is acidified in an aqueous acidic medium and then dried at low temperature. While drying temperatures of about 200° C. are acceptable for physical dewatering of the clay catalyst, it is preferred that a drying temperature lower than 100° C. be used, and preferably lower than 50° C. Dewatering at these lower temperatures may be carried out either by lyophilisation or by vacuum drying, or treating with a hydrophilic solvent such as alcohol or ketone.

According to a second process of acid treatment, the clay is treated with an ammonium salt followed, for example, by calcination, preferably at a low temperature, to eliminate ammonia and leave on the clay only the protons H+ originating from the ammonium salt. Calcination is preferably carried out at a temperature less than or equal to 500° C. and more preferably less than or equal to 400° C.

If desired, after one or more of the acid treatment processes, the clay may be treated with an alcohol, for example methanol or isopropanol, or with a ketone, such as acetone, and then dried.

The acid which is to undergo anhydridation is then contacted with the previously treated clay inside a reactor vessel preferably in the presence of a solvent selected from aromatic organic solvents which may be halogenated, such as toluene, xylene or chlorobenzene, and chlorinated aliphatic solvents.

To carry out the process according to the invention more expediently, the amount by weight of acid which is to undergo anhydridation is preferably calculated to be within the range of one to twenty times the amount of clay used. The acid to undergo anhydridation may be introduced continuously or in stages. Insofar as the process can be exploited continuously, the calculated quantity of acid in relation to clay can be significantly higher. A weight ratio of solvent to acid within the range of 20:1 to 150:1 is also preferred.

Examples of acids which can undergo anhydridation include:

aliphatic dicarboxylic acids, cycloaliphatic dicarboxylic acids, aromatic polycarboxylic acids.

Among the aliphatic dicarboxylic acids, it is possible to use saturated or unsaturated, linear or branched acids having preferably four to eight carbon atoms. Preferred acids include succinic acid, itaconic acid, maleic acid and glutaric acid. More preferably, aliphatic acids in which the principal chain is saturated and contains four carbon atoms are preferred. In this category, there may be mentioned succinic acid, itaconic acid and maleic acid. Itaconic acid is most preferably used.

Among cycloaliphatic dicarboxylic acids, saturated or partly unsaturated acids may be used. Nevertheless, the use of saturated acids is preferred. In this category there may be mentioned cyclohexenedicarboxylic acid and cyclohexanedicarboxylic acid.

Among the aromatic polycarboxylic acids, the aromatic dicarboxylic acids are preferably used. In this category there may be mentioned phthalic acid, trimellitic acid, trimesic acid, pyromellitic acid and prehnitic acid. Acids which are substituted by various groups which do not influence the ring structure of the molecule may also be used in the process of the invention.

When itaconic acid is used, the anhydride obtained can exhibit a selectivity above 90% and a selectivity of citraconic acid below 5%.

The reaction between the clay and the acid is preferably carried out at a temperature in the range of 80° C. to 200° C. and more preferably in the range of 100° C. to 150° C. for dicarboxylic acids. It is preferably carried out at atmospheric pressure.

The product obtained in the process of the present invention, i.e., the anhydride, can be free from metallic salts and particularly from aluminum in contrast with the product obtained by the process described in the publication which appeared in J. Chem. Research where there is a risk of the occurrence of contamination by an aluminum salt. This degree of purity is often essential because these anhydrides are important intermediates for the pharmaceutical and phytopathological industries (see U.S. Pat. No. 4,487,777, French Patents Nos. 2,466,450 and 2,480,600). They can also be used in the polymer industry (U.S. Pat. No. 4,480,125) where purity is an essential criterion.

The following examples further illustrate preferred embodiments of the present invention. The examples should in no way be considered limiting, but are merely illustrative of the various features of the present invention.

Abbreviations used in the series of examples have the following meanings:

TT=conversion ratio=% itaconic acid converted,
RT=yield of anhydride formed relative to acid converted.

EXAMPLE 1 a) Description of clay:

The catalyst used was a clay of the montmorillonite type with acid properties (Ref.: Product KSF from Sud-Chemie (Munich), (W. Germany).

b) Clay activation treatment: KSF—HCl—MeOH

Into a 1-liter glass beaker, equipped with a magnetic stirrer, were successively added 800 ml water, then sufficient concentrated hydrochloric acid to obtain a pH of 2.5, then 5 g of clay KSF. If the pH changes after the clay has been added, readjustment is made to a pH of 2.5.

The suspension was stirred for 1 hour at 25° C. The clay was recovered by filtration through sintered glass and washed with deionized water and placed in suspension again in 400 ml MeOH. After stirring for 1 hour and 30 minutes at 25° C. the clay was isolated by filtration through sintered glass, washed with methanol and dried for 16 hours at 40° C. at 100 mm Hg pressure.

c) Use of the KSF—MeOH catalyst in the anhydridation reaction

Into 1 100 ml glass Woulff reaction vessel having a central stirrer, a Vigreux distillation column (with a separator at the head with conveyance of the toluene water azeotrope over a column of 3A molecular sieves and recycling of toluene via a siphon), a 20 ml dropping funnel, a gas inlet and a heating system, 2 g itaconic acid, 0.5 g catalyst, (prepared as in 1b) and 50 to 55 ml toluene were added under an atmosphere of argon. The mixture was heated under reflux for 7 hours.

After reaction, the contents were allowed to cool to ambient temperature. The catalyst was recovered by filtration on sintered glass and washed with 4×30 ml acetone (with possible recovery of surplus itaconic acid). The filtrates were placed under reduced pressure (rotating evaporator provided with an oil pump) at 40° C., to remove the solvents.

Itaconic acid as well as itaconic anhydride and citraconic anhydride were analyzed by PMR-$^1$H (360 MHz). A special integration technique gives the composition of different components to within plus or minus 0.25%. The conversion ratio of itaconic acid was 93%, and the selectivities of itaconic anhydride and citraconic anhydride were, respectively, 94% and 5%.

EXAMPLE 2 (comparative)

Production of a clay exchanged with $Al^{+3}$.

5 g TONSIL 13 (alkaline montmorillonite ($Ca^{+2}$, $Na^+$)) marketed by Sud-Chemie were added gradually to a 0.24 M solution of $AlCl_3$ in water, with vigorous stirring at a temperature of 25° C. These conditions were maintained for 30 minutes. After centrifuging (5,200 rpm for 8 minutes) the solid was washed twice with 80 ml deionized water, each washing being followed by centrifuging. The TONSIL 13-$Al^{+3}$ obtained was dried for 17 hours at 80° C.

Use of TONSIL 13-$Al^{+3}$ in the anhydridation reaction.

The procedure of Example 1 was followed, except for using clay exchanged with $Al^{+3}$ as catalyst. The conversion of itaconic acid was 62% and the selectivities of itaconic anhydride and citraconic anhydride were respectively, 91% and 7%.

EXAMPLE 3

The procedure of Example 1 was followed using the same clay treated with aqueous HCl (pH=2.5) identified as KSF—CHl. Conversion of itaconic acid was 76% and the selectivities of itaconic anhydride and citraconic anhydride were respectively, 92% and 3%.

EXAMPLE 4

The procedure of Example 1 was followed using the same clay (KSF) but untreated. Conversion of itaconic acid was 9% and the selectivities of itaconic anhydride and citraconic anhydride were respectively, 67% and 43%.

EXAMPLES 5 TO 8

These examples describe the use of various acids for acidifying (treating) the clay and of various organic solvents for dispersing (treating) the clay after acidification, but before contact with the acid which is to undergo anhydridation. After treatment with the organic solvent listed in Table 1, the clay was also dried prior to contact with the acid which is to undergo anhydridation. They were used under the conditions as in Example 1 but at stage c) 1 g of catalyst was introduced instead of 0.5 g as in Example 1. The results are shown in Table 1.

TABLE 1

| EX. NO. | MONTMORILLO-NITE CLAY (GRADE REF) | ACID | SOLVENT | TT (%) ITACONIC ACID | RT (%) ITACONIC ANHYDRIDE | RT (%) CITRACONIC ANHYDRIDE |
|---|---|---|---|---|---|---|
| 5 | KSF | HCL | $CH_3OH$ | 96 | 95 | 2 |
| 6 | KSF | $F_3CSO_3H$ | $CH_3OH$ | 96 | 90 | 2 |
| 7 | K10 | $HNO_3$ | $(CH_3)_2 C = 0$ | 94 | 90 | 3 |
| 8 | K10 | $H2SO4$ | $(CH3)2 C = 0$ | 95 | 90 | 4 |

EXAMPLE 9 TO 11

These examples describe the use of different organic solvents which were used to bring itaconic acid into contact with clay KSF—HCl Methanol as prepared in Example 1. The results are shown in Table 2.

TABLE 2

| | | | | TT ITA- | RT | |
| Ex. No. | T ° C. | t h | SOL-VENT | CONIC ACID % | ITACONIC ANHYDRIDE | CITRACONIC ANHYDRIDE |
|---|---|---|---|---|---|---|
| 9 | 111 | 3 | toluene | 98 | 96 | 1 |
| 10 | 138 | 1.5 | xylenes | 97 | 92 | 2 |
| 11 | 138 | 0.7 | " | 96 | 97 | 1 |

EXAMPLES 12 TO 14

These examples describe the use of clays other than KSF or K10 used in the preceding examples, but treated one or more times with different acids and with different alcohols or ketones (cf. the following Table 3).

TABLE 3

| Ex. | Type of clay | Trade name | Acid | Alcohol or ketone | TT Itaconic acid | RT Itaconic anhydride | RT Citraconic anhydride |
|---|---|---|---|---|---|---|---|
| 12 | Montmorillonite | VOLCLAY | $H_3PO_4$ | $i.C_3H_7OH$ | 33 | 68 | 14 |
| 13 | Montmorillonite | TONSIL OPTIMUM FF | HCl | $CH_3OH$ | 97 | 93 | 2 |
| 14 | Montmorillonite | COPISIL D4 | HCl | $CH_3OH$ | 14 | 46 | 18 |

EXAMPLES 15 TO 23

These examples illustrate anhydridation of acids other than itaconic acid.

In each example the following quantities were employed:

16.7 mmol substrate, 60 ml solvent of the type shown in each table, 0.5 g to 2 g catalyst.

The catalyst was produced according to the procedure described in Example 1 (a to c).

The reaction temperatures and reaction periods are given in the following Tables 4 and 5:

TABLE 4

Results of anhydridation in toluene
Temperature: 110° C.
Period of reaction: 3 hours
Weight of catalyst: 0.5 g

| Ex. | Catalyst | Substrate | TT(%) | Product obtained | RT(%) |
|---|---|---|---|---|---|
| 15 | KSF—HCl—MeOH | itaconic acid | 96 | itaconic anhydride | 95 |
| 16 | KSF—HCl—MeOH | phthalic acid | 66 | phthalic anhydride | 99 |

TABLE 5

Results of anhydridation in xylene
Temperature: 140° C.
Period of reaction: 0.8 to 1 hour
Weight of catalyst: 0.5 g

| Ex. | Catalyst | Substrate | TT (%) | Product obtained | RT (%) |
|---|---|---|---|---|---|
| 17 | KSF—HCl—MeOH | itaconic acid | 96 | itaconic anhydride-derived diketone | 97 |
| 18 | TONSILE OPTIMUM FF | succinic acid | 95 | 2,5-hexanedione | 92 |
| 19 | KSF—HCl—MeOH | glutaric acid (HO₂C-(CH₂)₃-CO₂H) | 28 | glutaric anhydride | 86 |
| 20 | KSF—CHl—MeOH | cis-4-cyclohexene-1,2-dicarboxylic acid | 73 | 1,2-diacetyl-4-cyclohexene | 100 |
| 21 | KSF—HCl—MeOH | cyclohexene-dicarboxylic acid | 100 | 1,2-diacetylcyclohexane | 100 |

Results of anhydridation in mesitylene(1,3,5-trimethylbenzene)
Temperature 165° C.

| Ex. | Catalyst | Weight of catalyst (g) | Substrate | TT (%) | Period (h) | Product | RT (%) |
|---|---|---|---|---|---|---|---|
| 22 | KSF—HCl—MeOH | 1 | benzene-1,2,4-tricarboxylic acid | 87 | 1 | 1,2-diacetylbenzene | 97 |

TABLE 5-continued

| 23 | KSF—HCl—MeOH | 2 | benzene-1,2,4,5-tetracarboxylic acid (HO₂C, HO₂C, CO₂H, CO₂H substituents) | 36 | 6 | 1,2,4,5-tetraacetylbenzene | 64 |

We claim:

1. A method for producing an acid anhydride wherein said anhydride is glutaric anhydride, succinic anhydride, cyclohexene dicarboxylic acid anhydride, cyclohexane dicarboxylic acid anhydride, phthalic anhydride or pyromellitic anhydride, which method comprises bringing into contact, for a period of time sufficient to produce an acid anhydride, an acid precursor of said anhydride which is to undergo anhydration and a clay having a tetrahedron-octahedron-tetrahedron structure which has undergone one or more treatments by one or more compounds capable of providing an $H^+$ ion to the clay and which has not been treated, with a metal salt.

2. The process of claim 1, wherein said one or more compounds is an acid.

3. The process of claim 1, wherein said one or more compounds is an ammonium salt and further wherein ammonia is eliminated from said clay after said ammonium salt treatment to leave on the clay only the protons H+ originating from the ammonium salt.

4. The process as claimed in claim 3, wherein the clay is selected from the class of smectites.

5. The process as claimed in claim 4, wherein the clay in a montmorilonite.

6. The process as claimed in claim 2, wherein the one or more acid treatments are carried out using at least one acid wherein said acid is hydrochloric acid, sulfuric acid, nitric acid, perchloric acid, phosphoric acid or trifluoromethanesulfonic acid.

7. The process as claimed in claim 2, wherein the one or more acid treatments are carried out with a quantity of acid expressed in milliequivalents which is greater than or equal to the exchange capacity of the clay.

8. The process as claimed in claim 2, wherein after the one more acid treatments, a treatment is carried out using a ketone or an alcohol wherein said alcohol is methanol or isopropanol.

9. The process as claimed in claim 8, wherein the ketone is acetone.

10. The process as claimed in claim 2, wherein the acid which is to undergo anhydridation is brought into contact with the clay in the presence of a solvent wherein said solvents are organic aromatic solvents, or chlorinated aliphatic solvents.

11. The process as claimed in claim 2, wherein the acid which is to undergo anhydridation is brought into contact with the clay in the presence of an organic aromatic solvent wherein said solvent is toluene, xylene or chlorobenzene.

12. The process as claimed in claim 10, wherein the quantity of solvent used is such that the weight ratio of solvent to acid which is to undergo anhydridation is in the range 20:1 to 150:1.

13. The process as claimed in claim 2, wherein the reaction temperature is in the range of from 80° C. to 200° C.

14. A method of using an acidified clay catalyst to form an anhydride wherein said anhydride is glutaric anhydride, succinic anhydride, cyclohexene dicarboxylic acid anhydride, cyclohexane dicarboxylic acid anhydride, phthalic anhydride or pyromellitic anhydride, said method comprising the step of bringing into contact, for a period of time sufficient to produce said anhydride, a polyacid which is a precursor of said anhydride which is to undergo anhydration and a clay catalyst which has been acidified in an aqueous acidic medium, and which has not been treated with a metal salt.

15. The method of claim 1 wherein said acid anhydride is glutaric anhydride.

16. The method of claim 1 wherein said acid anhydride is succinic anhydride.

17. The method of claim 1 wherein said acid anhydride is cyclohexene dicarboxylic acid anhydride.

18. The method of claim 1 wherein said acid anhydride is cyclohexane dicarboxylic acid anhydride.

19. The method of claim 1 wherein said acid anhydride is phthalic anhydride.

20. The method of claim 1 wherein said acid anhydride is pyromellitic anhydride.

* * * * *